United States Patent
Kaul (10) Patent No.: US 8,529,124 B2
(45) Date of Patent: Sep. 10, 2013

(54) METHODS FOR GAS SENSING WITH SINGLE-WALLED CARBON NANOTUBES

(75) Inventor: Anupama B. Kaul, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 470 days.

(21) Appl. No.: 12/788,167

(22) Filed: May 26, 2010

(65) Prior Publication Data

US 2010/0308848 A1 Dec. 9, 2010

Related U.S. Application Data

(60) Provisional application No. 61/183,878, filed on Jun. 3, 2009.

(51) Int. Cl.
 *G01K 1/00* (2006.01)
 *G01K 7/00* (2006.01)

(52) U.S. Cl.
 USPC ........... 374/141; 374/100; 374/143; 374/163; 374/183; 374/1; 977/750; 977/953; 73/774

(58) Field of Classification Search
 USPC ................. 374/141, 142, 143, 100, 45, 109, 374/170, 178, 183, 163, 43, 1; 73/774; 977/750, 955, 953
 See application file for complete search history.

(56) References Cited

U.S. PATENT DOCUMENTS

| | | | |
|---|---|---|---|
| 6,946,197 B2 * | 9/2005 | Yadav et al. | 428/402 |
| 7,013,708 B1 | 3/2006 | Cho et al. | |
| 7,194,912 B2 * | 3/2007 | Jordan et al. | 73/774 |
| 7,389,696 B1 * | 6/2008 | Werner | 73/716 |
| 7,394,118 B2 | 7/2008 | Zhou | |
| 7,585,484 B2 * | 9/2009 | Liu et al. | 423/447.3 |
| 7,968,054 B1 * | 6/2011 | Li | 422/83 |
| 8,044,472 B2 * | 10/2011 | Kurtz et al. | 257/418 |
| 8,084,011 B2 * | 12/2011 | Suzuki et al. | 423/447.3 |
| 8,110,883 B2 * | 2/2012 | Ward et al. | 257/428 |
| 2003/0121764 A1 | 4/2005 | Yang et al. | |
| 2007/0045756 A1 * | 3/2007 | Chang et al. | 257/414 |
| 2008/0002755 A1 * | 1/2008 | Raravikar et al. | 374/100 |
| 2009/0165533 A1 | 7/2009 | Han et al. | |
| 2007/0086921 A1 | 10/2009 | Visel et al. | |
| 2010/0050745 A1 | 3/2010 | Liu et al. | |
| 2010/0056892 A1 | 5/2010 | Ben-Barak et al. | |
| 2010/0155698 A1 * | 6/2010 | Lieber et al. | 257/14 |
| 2010/0282245 A1 | 11/2010 | Star et al. | |
| 2010/0284002 A1 | 11/2010 | Li et al. | |
| 2008/0231361 A1 | 12/2010 | Ludwig | |
| 2010/0308848 A1 | 12/2010 | Kaul | |
| 2011/0051775 A1 * | 3/2011 | Ivanov et al. | 374/143 |
| 2011/0062418 A1 | 3/2011 | Ludwig | |
| 2011/0174079 A1 | 7/2011 | Manohara et al. | |
| 2011/0177493 A1 | 7/2011 | Lu | |
| 2012/0281729 A1 * | 11/2012 | Ou et al. | 374/187 |
| 2013/0031987 A1 * | 2/2013 | Beauvais et al. | 73/774 |

OTHER PUBLICATIONS

Iijima, S., Helical Microtubules of Graphitic Carbon, Nature 1991, 354: 56-58.

(Continued)

*Primary Examiner* — Gail Verbitsky
(74) *Attorney, Agent, or Firm* — Steinfl & Bruno, LLP (57) ABSTRACT

Methods for gas sensing with single-walled carbon nanotubes are described. The methods comprise biasing at least one carbon nanotube and exposing to a gas environment to detect variation in temperature as an electrical response.

17 Claims, 7 Drawing Sheets

(56) References Cited

OTHER PUBLICATIONS

Avouris, P., et al., Carbon Nanotube Electronics, Proceedings of the IEEE 2003, 91: 1772-1784.
Rueckes, T., et al., Carbon Nanotube-Based Nonvolatile Random Access Memory for Molecular Computing, Science 2000, 289: 94-97.
Sazonova, V., et al., A Tunable Carbon Nanotube Electromechanical Oscillator, Nature 2004, 431: 284-287.
Grow, R., et al., Piezoresistance of Carbon Nanotubes on Deformable Thin-film Membranes, Applied Physics Letters 2005, 86: 093104-1-093104-3.
Stampfer, C., et al., Fabrication of Single-Walled Carbon-Nanotube-Based Pressure Sensors, Nano Letters 2006, 6: 233-237.
Kong, J., et al., Nanotube Molecular Wires as Chemical Sensors, Science 2000, 287: 622-625.
Kaul, A.B., et al., Low Power, Wide Dynamic Range Carbon Nanotube Vacuum Gauges, Proceedings of the $21^{st}$ IEEE International Conference on MEMS 2008, 156: 1-4.
Bechtold, A., et al., Contacting Carbon Nanotubes Selectively with Low-ohmic Contacts for Four-Probe Electric Measurements, Applied Physics Letters 1998, 73: 274-276.
Martel, R., et al., Ambipolar Electrical Transport in Semiconducting Single-Wall Carbon Nanotubes, Physics Review Letters 2001, 87: 256805-1-256805-4.
Bockrath, M., et al., Luttinger-Liquid Behaviour in Carbon Nanotubes, Nature 1999, 397: 598-601.
Tans, S., et al., Individual Single-Wall Carbon Nanotubes as Quantum Wires, Nature 1997, 386: 474-477.
Nygard, J., et al., Electrical Transport Measurements on Single-Walled Carbon Nanotubes, Applied Physics A: Materials & Processing 1999, 69: 297-304.
Javey, A., et al., High-Field Quasiballistic Transport in Short Carbon Nanotubes, Physical Review Letters 2004, 92: 106804-1-106804-4.
Mann, D., et al., Ballistic Transport in Metallic Nanotubes with Reliable Pd Ohmic Contacts, Nano Letters 2003, 3: 1541-1544.
Nygard, J., et al., Quantum Dots in Suspended Single-Wall Carbon Nanotubes, Applied Physics Letters 2001, 79: 4216-4218.
Walters, D.A., et al., Elastic Strain of Freely Suspended Single-Wall Carbon Nanotube Ropes, Applied Physics Letters 1999, 74: 3803-3805.
Pop, E., et al., Negative Differential Conductance and Hot Phonons in Suspended Nanotube Molecular Wires, Physical Review Letters 2005, 95: 155505-1-155505-4.
1-Kaul, A.P. et al. "Carbon Nanotube Vacuum Gauges with Wide Dynamic Range." IEEE Transactions on Nanotechnlogy, Mar. 2009, vol. 8 (2), pp. 252-257.
1-Non-Final Office Action issued for U.S. Appl. No. 12/323,017, filed on Nov. 25, 2008 in the name of Harish Manohara et al. mail date: Oct. 7, 2011.
2-Final Office Action issued for U.S. Appl. No. 12/323,017, filed on Nov. 25, 2008 in the name of Harish Manohara et al. mail date: Feb. 1, 2012.
3-Final Office Action issued for U.S. Appl. No. 12/323,017, filed on Nov. 25, 2008 in the name of Harish Manohara et al. mail date: Jun. 7, 2012.
4-Notice of Allowance issued for U.S. Appl. No. 12/323,017, filed on Nov. 25, 2008 in the name of Harish Manohara et al. mail date: Nov. 9, 2012.
4-United States Patent issued for U.S. Appl. No. 12/323,017, filed on Nov. 25, 2008 in the name of Harish MANOHARA et al. Patent Number: 8,387,465; Issue Date: Mar. 5, 2013.
6-Kawano, T., et al. "An Electrothermal Carbon Nanotube Gas Sensor. Nano Letters." 2007, 7 (12), 3686-3690.
7-Mann, D., et al. "Thermally and Molecularly Stimulated Relaxation of Hot Phonons in Suspended Carbon Nanotubes." The Journal of Physical Chemistry B Letters, 2006, 110 (4), 1502-1505.
8-Kong, J., et al. "Synthesis of individual single-walled carbon nanotubes on patterned silicon wafers." Nature, 1998, vol. 395, 878-881.
9-Manohara, H.M., et al. "Carbon Nanotube Schottky Diodes Using Ti-Schottky and Pt-Ohmic Contacts for High Frequency Applications." Nano. Lett., 2005, 5 (7), 1469-1474.
10-Robinson, A.M., et al. "A thermal conductivity microstructural pressure sensor fabricated in standard complimentary metal-oxide semiconductor." Rev. Sci. Instrum., 1992, vol. 63 (3), 2026-2029.
11-Alvesteffer, W.J., et al. "Miniaturized thin film thermal vacuum sensor." J. Vac. Sci. Technol., 1999, vol. 13 (6), 2980-2985.
12-Naeemi, A., et al. "Physical modeling of temperature coefficient of resistance for single- and multi-wall carbon nanotube interconnects." IEEE Electron Dev. Lett., 2007, vol. 28 (2), 135-138.
13-Kong, J. et al. "Quantum interference and ballistic transmission in nanotube electron waveguides." Phys. Rev. Lett., 2001, vol. 87 (1), 106801-1-4.
14-Zhou, C. et al. "Intrinsic electrical properties of individual single-walled carbon nanotubes with small band gaps." Phys. Rev. Lett., 2000, vol. 84 (24), 5604-5607.
15-Jang, W.Y. et al. "Electrical characterization of individual carbon nanotubes grown in nanoporous anodic alumina templates." Appl. Phys. Lett., 2004, vol. 84 (7), 1177-1179.
16-Hsiou, Y.F., et al. "Controlled placement and electrical contact properties of individual multiwalled carbon nanotubes on patterned silicon chips." Appl. Phys. Lett., 2004, vol. 84 (6), 984-986.
17-Tans, S., et al. "Individual single-wall carbon nanotubes as quantum wires." Nature, 1997, vol. 386, 474-477.

* cited by examiner

METHODS FOR GAS SENSING WITH SINGLE-WALLED CARBON NANOTUBES

CROSS REFERENCE TO RELATED APPLICATIONS

The present application claims priority to U.S. Provisional Application No. 61/183,878 filed on Jun. 3, 2009 and incorporated herein by reference in its entirety. The present application is related to U.S. application Ser. No. 12/323,017, filed Nov. 25, 2008, which is incorporated herein by reference in its entirety.

STATEMENT OF FEDERAL SUPPORT

The invention described herein was made in the performance of work under a NASA contract, and is subject to the provisions of Public Law 96-517 (35 USC 202) in which the Contractor has elected to retain title.

FIELD

The present disclosure relates to carbon nanotubes. More in particular, it relates to methods for gas sensing with single-walled carbon nanotubes.

BACKGROUND

Since their discovery more than a decade ago [see reference 1] a plethora of electronic devices have been demonstrated using carbon nanotubes (CNTs), such as CNT-based FETs [see reference 2], memory elements [see reference 3], and tunable oscillators [see reference 4]. Gas sensing is another area of active research, where piezoresistance in single-walled-nanotubes (SWNTs) has been employed for applications such as pressure sensing [see references 5, 6] or where semiconducting nanotubes have been used for the detection of toxic gases such as nitrous oxide or ammonia [see reference 7].

DETAILED DESCRIPTION

Embodiments of the present disclosure are directed to methods using a carbon nanotube thermal-conductivity-based pressure or gas sensor, which utilizes diffusively contacted single-walled-nanotubes (SWNTs). Low temperature electrical transport measurements of these tubes indicate a thermally activated hopping mechanism for electron localization. A negative differential conductance regime is also detectable in suspended tubes at high bias voltages. According to results obtained by Applicants, the pressure or gas sensitivity increased more dramatically as the bias power is increased up to 14 µW. Exemplary applications of such devices are pressure sensors, as well as devices for the chemical identification of species having differing gas thermal conductivities, which include applications as miniaturized leak detectors or gas chromotographs.

The difference in thermal conductivities of nitrogen compared to hydrogen, for example, provides the ability to differentiate the two gas species using the thermal conductivity principle. This identifying mechanism is applicable to any gas that has a distinct thermal conductivity, including the hydrocarbons that are associated with biological activity. Conventional thermal conductivity gauges (e.g. Priani gauges) lend themselves to applications such as leak detectors or in gas chromatographs for identifying various gas species. However, these conventional gauges are physically large, operate at high power and have a slow response time. Several embodiments of the present disclosure would provide benefits of significantly reduced size and compactness, fast response time, low power operation and low-cost manufacturing since the devices can be, e.g., batch-fabricated using Si integrated-circuit (IC) process technology.

When a two-dimensional (2D) graphene sheet that comprises of a hexagonal arrangement of monolayer thick carbon atoms, is rolled into a cylinder, a one-dimensional (1D) form of carbon results, namely "single-walled carbon nanotubes" (SWNTs), which have a typical diameter of 1-2 nm. The conduction properties of SWNTs are intimately tied to the nature of the electrical contact between the CNT and the metal electrode, as well as intrinsic conduction within the tube body. In the absence of electron scattering and ideal electrical contacts, the conductance in SWNTs approaches the quantum limit characteristic of 1D systems, specifically $h/4e^2 \sim 6.5$ k$\Omega$, where e is the electron charge and h is Planck's constant. Metal contacts to the tubes give rise to an additional contact resistance $R_c$. The presence of scattering centers, such as defects, within the tube body give rise to another source of resistance $R_s$ that depends on the mean-free path and the length of the tube. The total resistance R is thus the sum of these three contributions, specifically $R=h/4e^2+R_c+R_s$. In practical situations however, $R_c$ and $R_s$ can be high and will dominate the overall contribution to the total resistance R. In this case the tubes are referred to as being "diffusively contacted" since $R>>h/4e^2$ (the quantum conductance).

Embodiments of the present disclosure are directed to a gas or chemical sensor, and methods of using the sensor, that operates on the principle of thermal exchange between a voltage-biased CNT and the surrounding gas, where the rate of heat removal by the surrounding gas is a function of the pressure. The heat removal causes the temperature to change within the CNT which causes the resistance to also change that is then detected as a change in current. Since the amount of heat removed by the gas $E_g$ is directly proportional to the pressure P and the free molecule thermal conductivity $\Lambda_t$ of the gas in the viscous flow regime [see reference 8], the same effect can also be used to differentiate gaseous chemical species For instance, hydrogen and nitrogen have vastly different thermal conductivities, with $\Lambda_t \sim 168.3$ mW/m-K and 25.8 mW/m-K, respectively. Commonly known thermal conductivity gauges such as Pirani gauges are used for pressure sensing, but can also be used in gas chromatographs for chemical identification, as well as for leak detectors.

The SWNTs are amenable as chemical sensors in miniaturized systems because of their small feature size or footprint, unlike conventional systems which are physically large (e.g. pirani gauges and gas chromatographs). The small size and ability to operate at low powers (nanowatts–microwatts) of the SWNT-based chemical sensors makes them non-invasive to the sensing environment, unlike the conventional sensors which operate at high-power (>milliwatts) and thereby release substantial heat, perturbing the local environment. The SWNTs also offer advantages due to their unique electrical and mechanical conduction properties. For example, the presence of a negative differential conductance (NDC) regime in suspended SWNTs gives them unique thermal characteristics due to the large optical phonon density in such materials not seen in other materials. In addition, the defects that may be present in the tubes give rise to a thermally activated hopping mechanism for electron transport with an activation energy Ea measured to be ~39 meV; this leads to a large temperature coefficient of resistance which increases sensitivity of the detector. In addition, the exceptional mechanical properties of the tubes (ability to tolerate a large degree of mechanical strain) which arises from the $sp^2$-bonding in SWNTs, makes SWNT-based chemical sensors more physically robust and increases the lifetime of the detector. Other materials in such a suspended geometry cannot sustain large mechanical strains due to their atomic bonding, which makes them more prone to fracture and not as robust. As used herein, the terms "tube," "CNT," "carbon nanotube," and "SWNT" are used interchangeably.

According to some of the embodiments of the present disclosure, sensing methods are described. The method comprising providing at least one carbon nanotube and biasing the at least one carbon nanotube. The method further comprising exposing the at least one carbon nanotube to an environment where gas is adapted to be detected, whereby, in presence of the gas, heat is removed by the gas from the at least one carbon nanotube. The method further comprising varying pressure inside the environment with the gas, whereby temperature of the at least one carbon nanotube changes with variation of pressure, and detecting variation in temperature of the at least one carbon nanotube as an electrical response.

In an embodiment, biasing the carbon nanotubes occurs by connecting electrodes at end regions of the carbon nanotubes. In some embodiments, the carbon nanotubes and the electrodes are suspended and devoid of a substrate. Suspension can occur through critical point drying as well as other suspension methods known in the art. In some embodiments, the at least one carbon nanotube is voltage biased and the electrical response is a current response. In some embodiments, the electrical response is a voltage response.

In an embodiment, varying the pressure inside the environment with the gas comprises varying the pressure from a substantially ambient pressure to a substantially vacuum pressure.

In an embodiment, the variation in the temperature of the at least one carbon nanotube causes a resistance change in the at least one carbon nanotube, the resistance change being detected as a current response.

In an embodiment, the environment is a chamber containing the gas and the at least one carbon nanotube.

In an embodiment, the method is a gas sensing method. In another embodiment, the method is a chemical species sensing method to differentiate chemical species.

In an embodiment, the carbon nanotube is a single-walled carbon nanotube. In some embodiments, an array of carbon nanotubes may be used. In other embodiments, a bundle of carbon nanotubes may be used.

According to some of the embodiments of the present disclosure, a method of sensing is described. The method comprises exposing a sensor to an environment where gas is adapted to be detected and detecting variation in temperature of the single-walled carbon nanotube as an electrical response. The sensor comprises two terminals; a biasing source to the terminals; a single-walled carbon nanotube in electrical communication between the terminals; a calibration of measured electrical conductance of the single-walled carbon nanotube to magnitudes of vacuum about the single-walled carbon nanotube; and a current meter in electrical communication with the source of constant voltage, wherein, in presence of the gas, heat is removed by the gas from the sensor. In some embodiments, the biasing source is a source of constant voltage.

In an embodiment, the method is a method of sensing gas. In another embodiment, the method is a method of sensing a chemical species to differentiate chemical species. In an embodiment, the sensor is in an array. In another embodiment, the sensor is in a bundle.

In an embodiment, the sensor comprises a substrate supporting the two terminals. In an embodiment, the single-walled carbon nanotube is displaced from the substrate between the terminals. In some embodiments, the electrical response is a current response or a voltage response. In an embodiment, the single-walled carbon nanotube is 5 µm to 10 µm in length between the terminals. In some embodiments, the single-walled carbon nanotube is less than 5 µm in length between the terminals. In some embodiments, the single-walled carbon nanotube is greater than 10 µm in length between the terminals. In some embodiments, the electrical response is a current response.

Figure 1A:
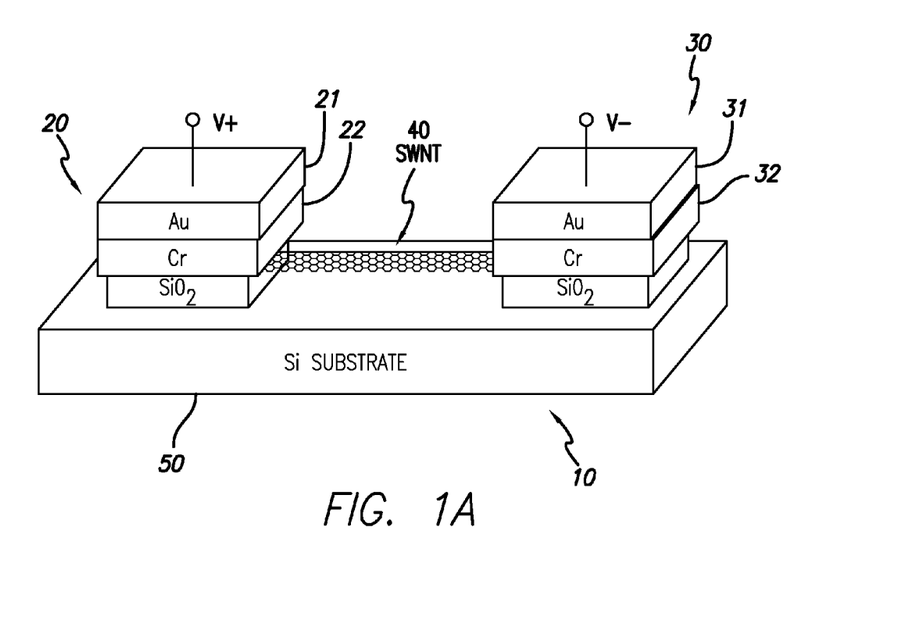
FIG. 1A shows a schematic diagram of a CNT gas pressure or chemical sensor in accordance with the present disclosure. In the example shown in the figure, Au/Cr electrodes (250 nm/5 nm) anchor the tube during exposure to 10:1 BHF for removing $SiO_2$ beneath the tubes. Critical point drying in an isopropyl alcohol (IPA) bath can be used for the final release.

FIG. 1a shows the device in operation which is comprised of a suspended SWNT biased with a voltage V+ and V− (or the ground electrode) at the 2 electrodes. The SWNT can be suspended to increase its sensitivity. This device is placed in a chamber and the current through the device is measured as the gas pressure is decreased from ambient (760 Torr to vacuum-levels ($10^{-6}$ Torr). The voltage in the SWNT is held fixed at V+ and V− in the left and right electrodes, respectively, with the use of a semiconductor parameter analyzer (such as the HP4156C) while the parameter analyzer samples the current through the SWNT as the pressure (and hence temperature) changes. The current may be sampled at 1 second intervals at fixed bias voltage. ICS data acquisition software may be used with a computer interfaced to the parameter analyzer. In some embodiments, an array of SWNTs could be utilized. In other embodiments, a bundle of SWNTs could be utilized.

Devices as mentioned above and methods to manufacture such devices are described in the present disclosure, where, in accordance with some embodiments, the SWNTs are released to minimize solid-state heat conduction through the substrate, in order to enable sensitivity to higher vacuum levels (~$1\times10^{-6}$ Torr). In other embodiments, the SWNTs are not released from the substrate. The terms, "released" and "suspended," are used interchangeably in the present disclosure. Likewise, the terms, "unreleased" and "unsuspended," are used interchangeably in the present disclosure. Low temperature electrical transport measurements of the SWNTs are also described in the present disclosure. These low temperature electrical transport measurements of SWNTs are done in order to interpret the gas pressure response of the tubes. Electrical transport characteristics of suspended tubes are also described in the present disclosure in the exemplary context of phonon relaxation mechanisms in 1-D systems, where a negative differential conductance (NDC) regime is also present in the suspended tubes at high bias voltages.

FIG. 1A shows an example of a CNT pressure sensor (10) in accordance with an embodiment of the present disclosure, where two terminal anchoring connections (20, 30) are made to the tube (40) at either end with electrodes (21-22, 31-32) (e.g., Au/Cr 250 nm/5 nm electrodes patterned by lift-off). Tube growth can be obtained, by way of example, with thermal CVD at 800° C. in a methane and hydrogen ambient. In some embodiments, an array of SWNTs could be utilized in the pressure sensor. In other embodiments, a bundle of SWNTs could be utilized in the pressure sensor.

After patterning the electrodes, some of the devices can be annealed in a hydrogen ambient at 300° C. to reduce contact resistance. Other devices remain unannealed so that the pressure response may be compared between annealed and unannealed devices. Low temperature terminal measurements can be conducted by placing the wire-bonded devices on a probe stick equipped with a thermocouple for temperature determination.

Cooling is done to determine the temperature coefficient of the sensor. When the SWNT sensor is in operation, it locally cools. By doing controlled low temperature measurement to see how the resistance varies, pressure data can be interpreted. Cooling can be induced by lowering the probe stick in the vapor above the liquid in a helium Dewar, in order to shed insight on the nature of electrical transport through the tubes. The Si substrate (50) beneath the tubes can be removed using HF, followed by a final release step in a critical point dryer to minimize surface tension stress. The gas or pressure response of the unannealed or annealed and released or unreleased devices was performed in a bell jar equipped with mechanical pump which reduced the pressure from 760 Torr to ~35 mTorr, after which point a turbo pumped was used to further reduce the pressure to ~$10^{-6}$ Torr. The devices were usually immersed in nitrogen prior to each pump down cycle. More details of the measurement set-up are provided elsewhere. [See reference 9].

Figure 5:
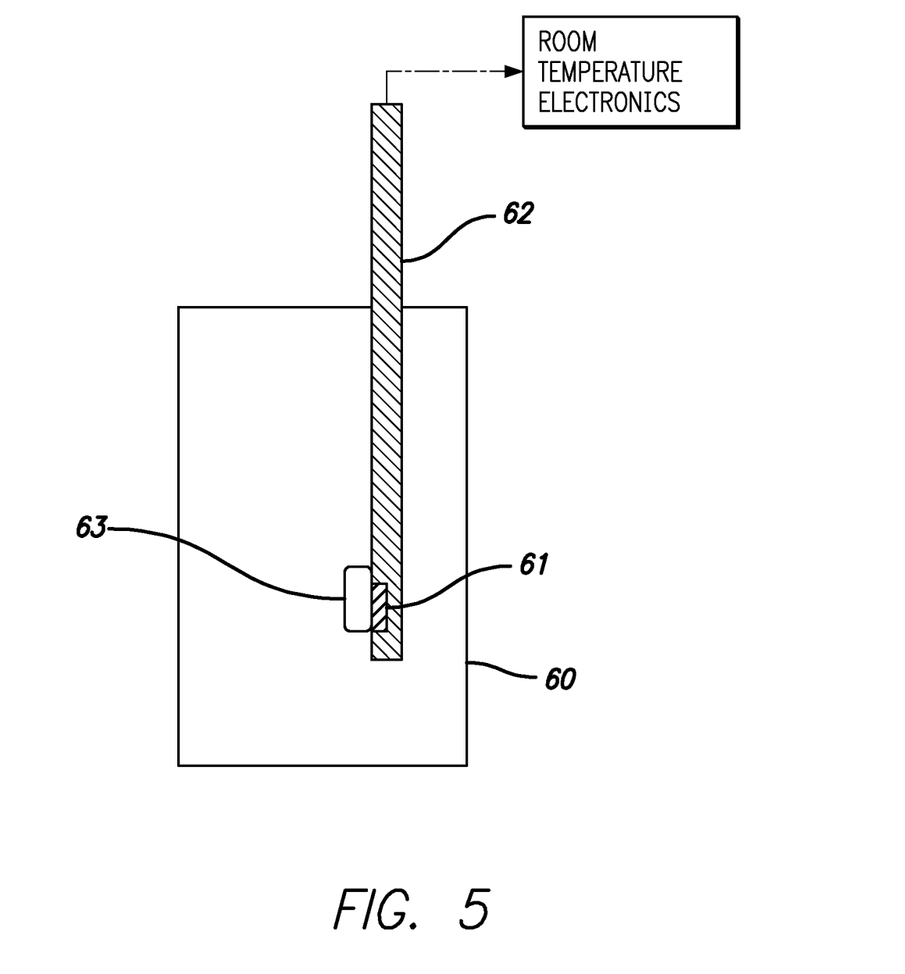
FIG. 5 shows a low temperature measurement setup for testing a device which uses a probe for cryogenic measurement carried out in a liquid helium (LHe) dewar.

FIG. 5 shows an example of a low temperature measurement in accordance with an embodiment of the present disclosure, where a probe (62) for cryogenic measurement is lowered into a liquid helium (LHe) dewar (60). The probe contains the device under test (DUT) (63) (i.e. a SWNT device such as that described in FIG. 1A) and a thermocouple (61) to sense the temperature as the probe is lowered into the dewar and cooled. The probe is further connected to room temperature electronics, as shown in FIG. 5. As the probe is lowered into the dewar, the vapor from the LHe bath causes cooling for the DUT. The temperature is measured with the thermocouple attached to the probe. The electrical data measurements may be made at the particular temperature from which the resistance is determined. If measurements are made at various temperatures, the resistance versus temperature data may be gathered.

According to an embodiment of the disclosure, Cr is used as a contact metal to the CNT. Such choice stems primarily from the inertness of Cr to HF, unlike Ti which etches easily in HF and would have caused the contacts to wash away upon release. In the Cr-contacted CNT devices according to such embodiment, contact resistances can range from 100's kΩ-10's MΩ. Post-growth treatment such as electron irradiation [see Reference 10] has shown to improve contacts, with annealing being a more commonly implemented technique. In other embodiments, the contact metal to the CNT could include Al, Ti, Nb, Au, Cr and combinations thereof. If it is not desired to release the devices (i.e., if enhanced sensitivity is not desired at lower pressures), the choice of metals to be used could include the above mentioned metals plus others, such as Mo, Pd, Pt, Sc, Ta, W, Hf, Zr and others known to those skilled in the art, since one does not need to be concerned about the metal not surviving the wet BOE etchant.

Figure 1B:
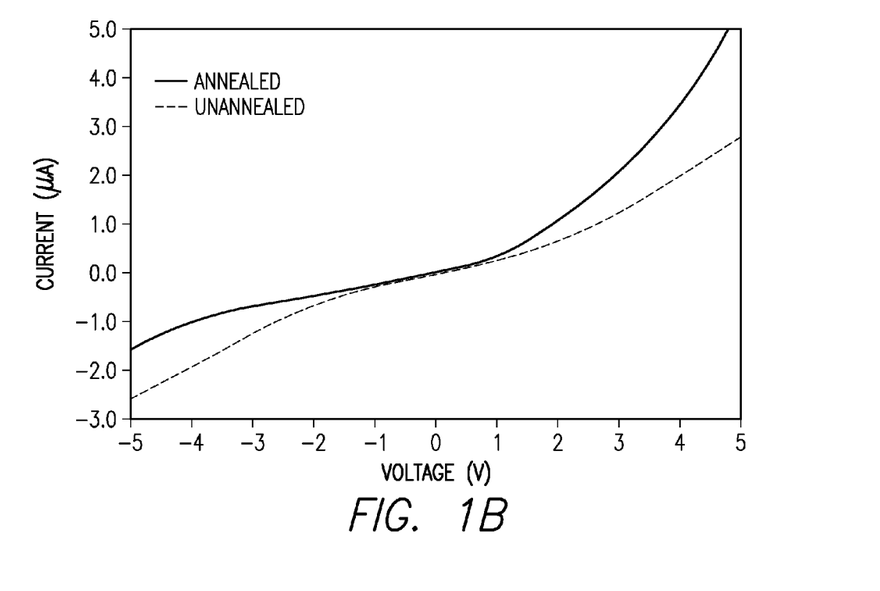
FIG. 1B is an I-V diagram showing the effect of annealing the Cr-contacted SWNT device at temperatures ~300° C. for 1 hour. The forward-biased resistance is reduced by a factor of ~2 (from ~2 M$\Omega$ to ~900 k$\Omega$).

Shown in FIG. 1B is an I-V characteristic of an embodiment of a Cr-contacted CNT device according to the disclosure before and after it was annealed at 300° C. for 1 hour. The contact resistance decreased by about a factor of two (from ~2 MΩ to ~900 kΩ) in the forward bias regime with annealing. In Ti contacted CNT devices, annealing at similar temperatures can decrease resistance by more than an order of magnitude. The fact that applicants did not observe as pronounced a decrease in contact resistance with annealing suggests little chemical reactivity between Cr and C at least at temperatures up to ~300° C., in contrast to Ti-contacted devices, where the formation of interfacial TiC is known as a mechanism for reduced resistances [see Reference 11]. While contact resistances with Cr according to the above embodiment were high, they were stable with time and did not show a large variation with aging. Cr is used if it is necessary to release the devices. The high contact resistance in the Cr-contacted devices is not necessarily an issue, but if lower contact resistances are necessary (e.g. to increase the magnitude of the currents), annealing to higher temperatures beyond 300° C. may be necessary. But Cr-contacted SWNTs have a reproducible resistance and are more stable with time which is important for applications.

Low Temperature Transport

The physical phenomena that rely on transport through the tubes, such as the use of CNTs as thermal conductivity gas or pressure sensors require some understanding of the nature of electrical transport. In order to elucidate the mechanism of transport in the tubes according to the present disclosure, the variation of electrical conductance G was measured from room temperature down to 50 K.

Figure 2A:
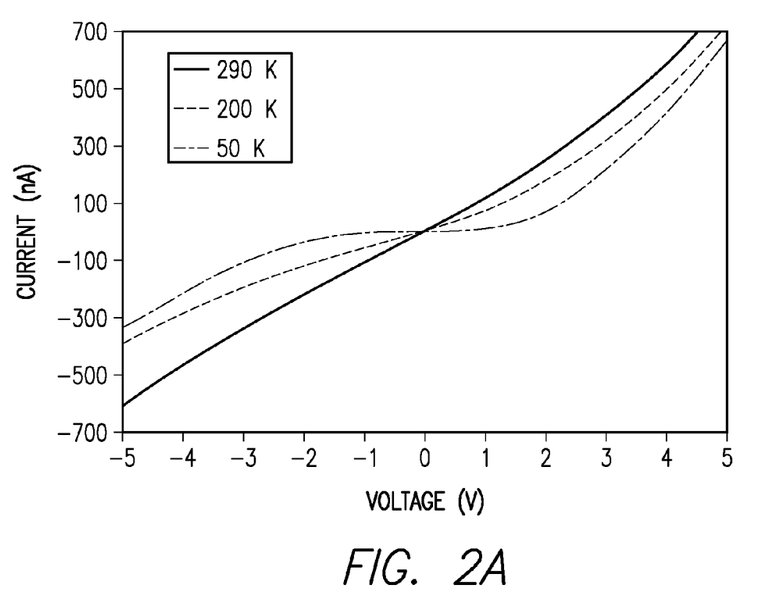
FIG. 2A shown an I-V characteristic of a SWNT device showing predominately linear characteristic at 290 K up to 5 V, with a non-linearity emerging at 50 K at low biases.
Figure 2B:
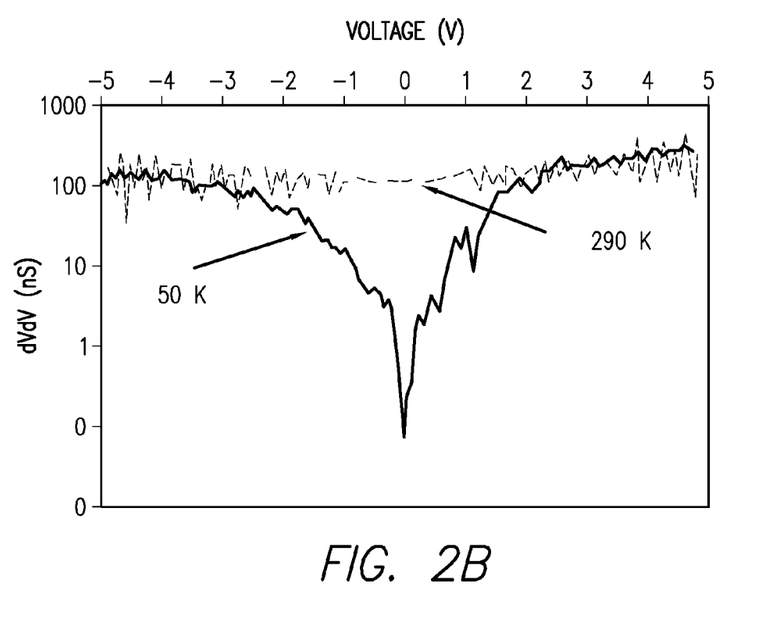
FIG. 2B shows that the zero-bias conductance is reduced by more than 3-orders of magnitude at 50 K, which converges to the room temperature conductance at large voltages.

Shown in FIG. 2A is an exemplary I-V characteristic of a device which was predominately linear at ~290 K up to 5 V. At 200 K, a slight non-linearity begins to arise at low bias voltages, which gets more pronounced at 50 K. In FIG. 2B, the conductance (dV/dt) at 290 K of the same device appears to be independent of the bias voltages, as expected, but at 50 K, a gap is evident for voltages <1.5 V. The conductance is suppressed by more than 3 orders of magnitude at zero volts, but converges to its room temperature value for high bias voltages (i.e. voltages 1.5v and higher). Operation of the device at high-bias voltages increases sensitivity.

Suppressed conductance at low temperatures under low bias conditions could arise from several mechanisms. Since the contacts are far from ideal, a Luttinger-Liquid behavior characteristic of electrons in one-dimensional (1-D) systems is highly unlikely, and in fact, a power law dependence of $G \prec T^\alpha$ ($\alpha$=0.33-0.38) did not provide a good fit to the data [see reference 12]. For low transparency contacts $$\left( T \ll 1 \text{ in } G = T \cdot \frac{4e^2}{h} \right)$$

the CNT is weakly coupled to the leads due to a potential barrier at the interface which can lead to coulomb blockade [see reference 13]. In such a case, the magnitude of the charging energy U is determined both by the device geometry and the nature of the tubes. If coulomb blockade is dominant here, a large charging energy, where $$U = \frac{e^2}{2C} > k_B T,$$

is observed since gap formation appears at temperatures as large as 50 K, where C is the capacitance that was computed to be as small as ~18.5 aF. While a potential barrier at the contacts can lead to coulomb blockade, a large charging energy could also result from defects within the nanotubes themselves, implying quantum dots in short segments of the tube [see reference 14].

Figure 2C:
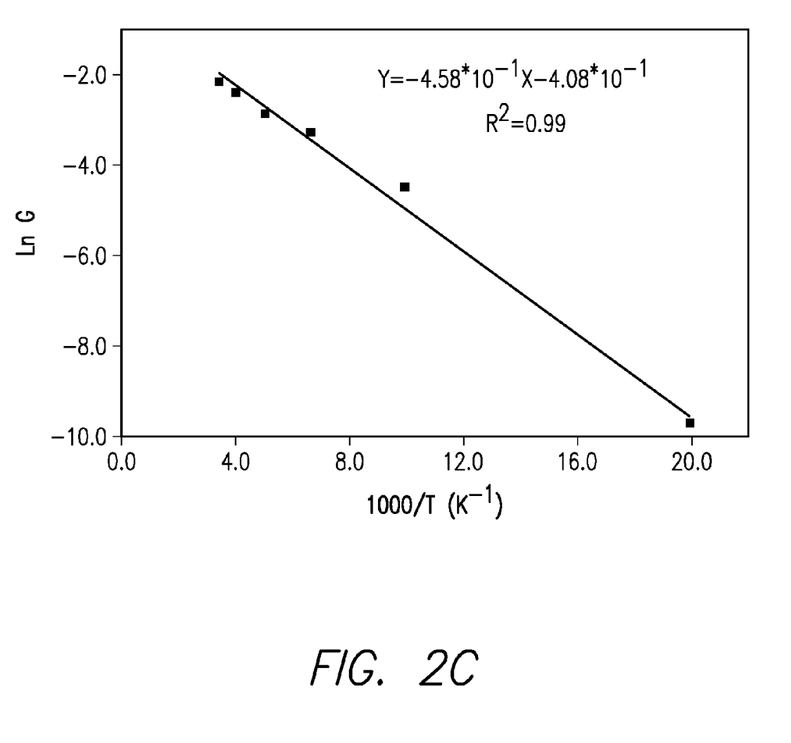
FIG. 2C shows a fit of Ln G~$-E_a/k_B T$ suggests a thermally-activated hopping mechanism for electron localization, where $E_a$ for the particular example shown in the figure was computed to be ~39 meV for electron hopping.

If defect density is large, the electrons get localized and conduction can happen through thermally activated hopping. Such a mechanism, with $$LnG \prec \frac{-E_a}{k_B T},$$

appeared to fit the data well for the Cr-contacted SWNTs according to an embodiment of the present disclosure, as illustrated in FIG. 2C, where $E_a$ is the activation energy. From this, a hopping energy of $E_a$~39 meV can be calculated for an embodiment of the device. According to an embodiment of the disclosure, the SWNTs (40) in the devices can have long lengths (5-10 μm) and electron-phonon scattering along the length of the tube is highly probable, since mean-free-path for CVD grown tubes have been measured to be as low as ~1 μm [see reference 15]. As used herein, the term "mean-free-path," refers to the average length an electron travels before it encounters a scattering event from a defect. Mean free paths for optical phonon scattering in SWNTs at high biases (>0.1 V) have been determined to be as low as 15 nm [see reference 16]. In addition, long SWNTs are more likely to have mechanical deformations (bends, etc.) which can also contribute to conductance suppression at low temperatures. These measurements suggest that a lumped effect involving both the contacts where tunnel barriers are highly probable, and the long tubes themselves where scattering from defects leads to electron localization, are both involved in determining the pressure response of the CNT thermal-conductivity-based gas or pressure sensors according to the disclosure. The device may be used at high bias voltages to increase sensitivity. The large contact resistance ($R_c$) and the long tubes suggest that the defects within the tubes will impact the scattering resistance ($R_s$) measured and both of these will then influence the temperature response of the devices.

Substrate Release

Figure 3A:
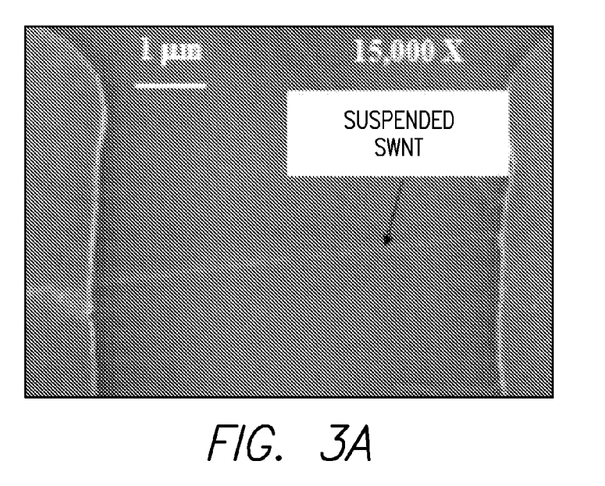
FIG. 3A shows a SEM image showing a fully suspended tube after release using critical point drying in an IPA bath. The trench depth for the particular example shown in the figure is ~310 nm.

According to an example of the present disclosure, in order to release the devices, the $SiO_2$ beneath the SWNTs was etched in 10:1 Buffered-HF (BHF) with an etch rate ~52 nm/min, which was followed by critical point drying. Nygard et al. [see reference 17] employed simple drying techniques after HF etching to release <1 μm long tubes by using the reduced surface tension of isopropyl alcohol (IPA) (21.7 mN/m) compared to that of distilled (DI) water (72.8 mN/m), whereas Walters et al. [see reference 18] utilized the even lower surface tension of tetramethylsilane (10.2 mN/m). For the long SWNTs used in the example discussed above which are more susceptible to surface tension stress upon wet-release, added precautions were taken that utilized critical point drying in an IPA bath, in order to minimize tube slippage. Shown in FIG. 3A is an SEM of a released device where the tube was completely suspended.

Figure 3B:
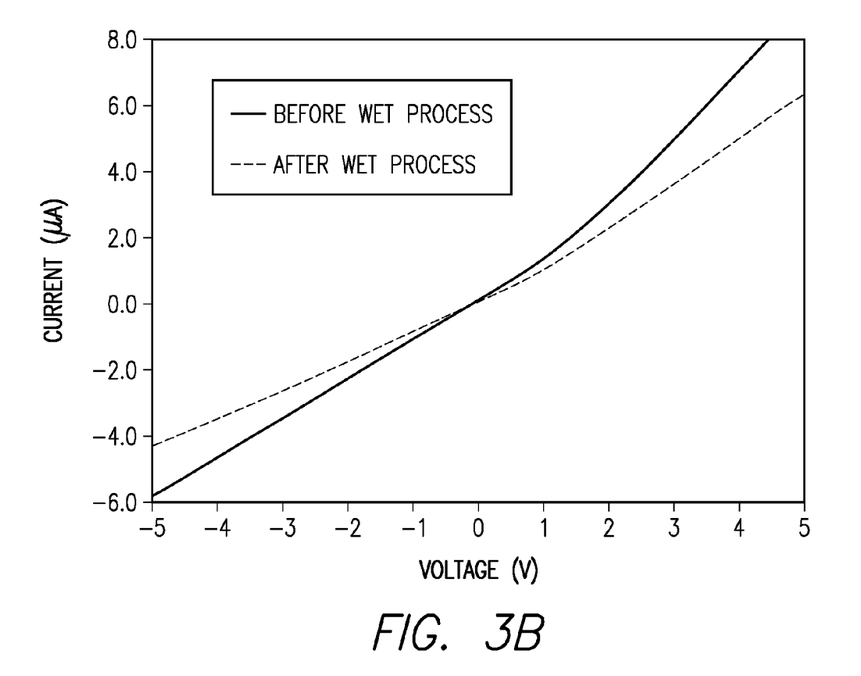
FIG. 3B shows an I-V characteristic for an exemplary 20 µm catalyst device which was taken before and after it was exposed to acetone, IPA and critical point drying only. Wet processing alone (without BHF) appears to reduce conductance, possibly due to strain induced at the contacts or by some of the tubes washing away.

The electrical yield of the example discussed above after release—defined by the number of electrically conducting devices—was >90%, but the resistances were always higher after release. The rise in resistance could be associated with the contacts where the tubes are likely to exhibit kinks that suppress conductance. It could also be due to HF damaging the SWNTs. Applicants' results suggest that wet-processing alone, comprising of exposure to water, IPA (isopropyl alcohol) and critical point drying, is partly responsible for conductance decreases, as shown by a representative I-V in FIG. 3B taken for a device with a 20 μm catalyst site. Besides strains at the contacts, wet processing could potentially cause loosely attached tubes to wash away, especially at large-area catalyst sites where the likelihood of multiple tubes is higher. While wet-processing appears to have a role to play in the observed conductance decrease, more work is necessary to fully characterize the extent to which HF damage is also involved. The process of releasing the devices with critical point drying is gentle enough that the tubes are sufficiently intact that there is still electrical conduction between the left and right electrodes.

Pressure Response

Figure 4A:
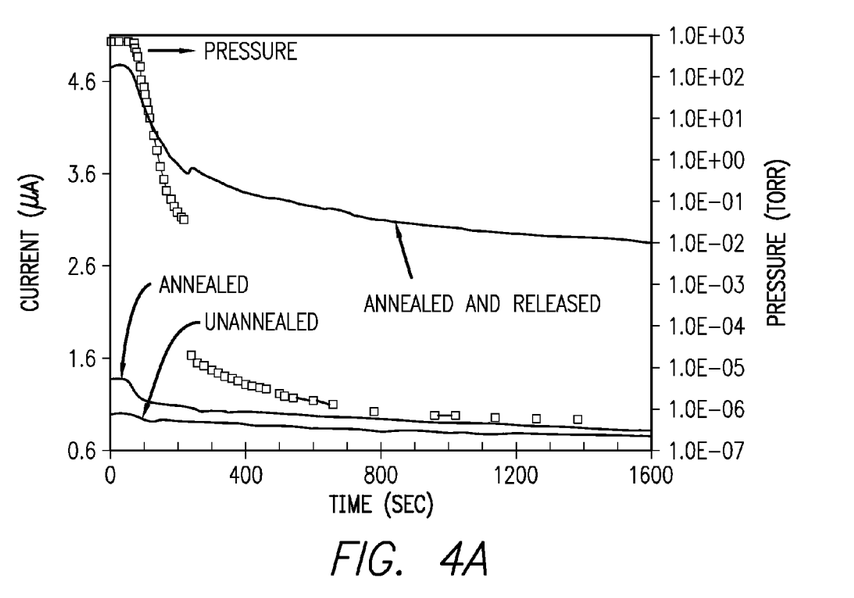
FIG. 4A shows an absolute current variation for the unannealed, annealed, as well as the annealed and released devices as a function of time/pressure at a bias power of ~2 µW. The pressure response of the unannealed and annealed devices saturates beyond ~100 sec. or ~1 Torr, but the released device shows a measurable conductance change down to ~$10^{-6}$ Torr.

Gas or pressure sensing response of the devices was measured using two terminal measurements of conductance with an HP 4156C parameter analyzer, while the devices were placed in a vacuum chamber and pumped down. A more detailed description of the measurement-set-up is given elsewhere [see Reference 8]. Shown in FIG. 4A is the pressure response for unannealed, annealed, as well as the annealed and released devices. In all three cases, the conductance of the CNT device decreased rapidly initially, after which point changes occur less rapidly. As pumping occurs, gas phase collisions cause thermal energy to be transferred to the gas, which results in local cooling, influencing the resistance of the current carrying element. Higher pressures generate higher collision rates and thus, greater cooling. Since the differential change of conductance with temperature is positive as can be deciphered from FIG. 2A $$\left(\text{i.e. } \frac{dR}{dT} < 0\right)$$

cooling would result in conductance suppression with decreasing pressure, as observed. Eventually, the gas-phase mean free paths become longer, and the response becomes less sensitive. For the unannealed and annealed device in FIG. 4A, the sensitivity is diminished beyond about 100 sec. (~1 Torr) but the released CNT gas sensor has a continued decrease in conductance well into the $10^{-6}$ Torr range. The data indicate that by removing part of the $SiO_2$ substrate underneath the current carrying element, sensitivity is increased into the lower pressure ranges since solid-state conduction through the substrate is minimized, leaving more of the heat to be propagated by the gas. Radiative losses are presumed to be minimal at the low operational temperatures (or power) of the devices.

Negative Differential Conductance (NDC)

Figure 4B:
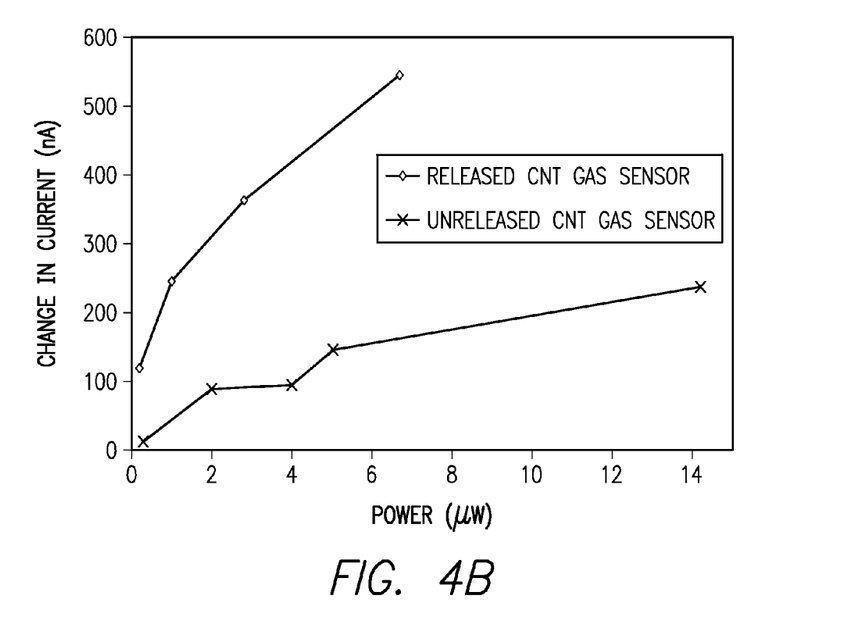
FIG. 4B shows the net current change from ~$5 \times 10^{-6}$ Torr to ~$8 \times 10^{-7}$ Torr for the released and unreleased CNT gas sensor as a function of bias power. The largest change in conductance is for released device as power is increased.

The increase in sensitivity after substrate removal is better illustrated in FIG. 4B which shows the net current change ($\Delta I$) for released and unreleased device in the pressure range of $\sim 5 \times 10^{-6}$ Torr to $\sim 8 \times 10^{-7}$ Torr. In both cases, $\Delta I$ increases with power but the released device has a three times larger change, where $\Delta I \sim 550$ nA at a bias of $\sim 6$ µW, compared to $\Delta I \sim 150$ nA for the unreleased device. While the increased current sensitivity with substrate removal can be explained on the basis of heat minimization through the substrate, the reduced dimensionality for phonon scattering in 1-D systems, in particular suspended SWNTs, can cause unique effects to arise at large bias voltages and power. At high fields, a large nonequilibrium optical phonon population exists in suspended SWNTs and their long relaxation times result in non-isothermal conditions along the length of the tube. Pop et al. [see reference 19] have iteratively obtained the I-V characteristic of both suspended and unsuspended SWNTs, by modeling the occupation probability of both optical and acoustic phonons at high biases, according to $$I = \frac{V}{R(V, T)}$$

where, $$R(V, T) = R_c + \frac{h}{4e^2} \frac{[L + \lambda_{eff}(V, T)]}{\lambda_{eff}(V, T)} \quad (1)$$

Here, $R_c$ is the contact resistance, L is the length of the nanotube and $\lambda_{eff}$ is the sum of the acoustic, optical (emission) and optical (absorption) mean free paths derived from the Bose-Einstein phonon distribution. This analysis showed that in unsuspended tubes the I-V characteristic increases monotonically at high voltages suggestive of isothermal conditions, since the substrate facilitates in the relaxation of optical phonons emitted through electron scattering. In contrast, the current in the suspended tube saturates and a NDC regime is encountered, which cannot be explained by velocity saturation (at ~5 kV/cm).

Figure 4C:
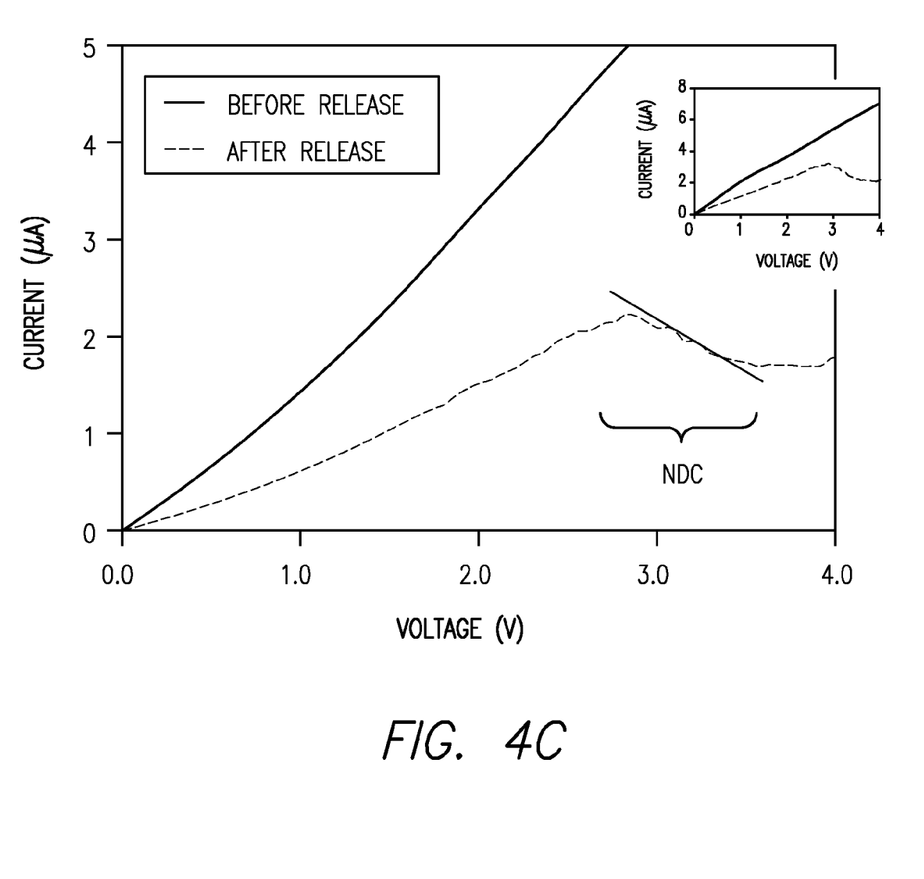
FIG. 4C shows the conductance of an unreleased SWNT device increases monotonically as the bias is increased, but after substrate removal, current saturation and a negative differential conductance (NDC) regime is observed in this device at high biases, which is attributed to the high optical phonon density. Inset shows a higher current scale.

NDC in SWNTs determines the temperature profile within suspended SWNTs. Applicants have observed NDC in the suspended SWNT devices as shown by the I-V characteristic in FIG. 4C, where the measurements were taken in air and at room temperature. The unreleased device shows a monotonic rise in conductance, while the current after release for the same device saturates at high bias, ~2.8 V in this case, and enters a NDC regime. A peak conductance $I_{peak}$, where $$I_{peak}(\mu A) = \frac{10}{L(\mu m)} \quad (2)$$

has been calculated and depends inversely on the length of the tube [see reference 19]. In the device shown in FIG. 4C, the experimentally observed $I_{peak}$ was ~2.1 µA which appears to be in rough agreement with the expected value since the electrode spacing (and hence tube length) for this device was ~6 µm. The measurements performed by Applicants show pressure or gas sensitivity increases as the bias voltage or power are increased, but the released devices showed a more pronounced effect with power, as shown in FIG. 4B. The large optical phonon density in suspended SWNTs at high fields with the long lifetimes may play an important role in determining the rate of temperature rise in the tubes, which can be exploited for their utility as thermal conductivity-based gas sensors.

The low temperature transport measurements of the tubes according to the present disclosure are suggestive of a thermally activated hopping mechanism causing electron localization, where the hopping energy was computed to be ~39 meV. Tunnel barriers at the contacts, as well as dissipation within the tubes arising from defects (bends, etc.) could both contribute to such a mechanism. Exemplary released devices appear to have a wide dynamic range (760 Torr-$10^{-6}$ Torr) compared to the unreleased devices, and a NDC regime was also observed in the released device that was discussed in terms of the high nonequilibrium optical phonon density in suspended SWNTs at high biases. CNT thermal-conductivity-based sensors can be useful for applications such as gaseous pressure sensing, chemical detectors such as in gas chromatographs or leak detectors, due to their low power operation, ultra-miniature size, fast response time, and their amenability for batch fabrication.

A possible application of the devices and methods according to the disclosure is use as leak detectors. For use as a leak detector, the CNT gas sensor will provide a background signal for air. When a gas such as Helium is placed in the area where the leak is to be measured, a large difference in the current signal will be noted compared to that of air, which is attributed to the large difference in the thermal conductivity of He compared to that of air.

A further application of the devices and methods according to the disclosure is use as gas chromatographs. Moreover, due to its miniature size, the sensor could be integrated within a micro-cavity to detect biological activity by measuring the outgassing rate of specific gaseous species such as the hydrocarbons, etc.

It is to be understood that the disclosure is not limited to particular configurations or the assembly, components or devices, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains.

The description set forth above is provided to give those of ordinary skill in the art a complete disclosure and description of how to make and use the embodiments of the assembly, components, devices, systems and methods of the disclosure, and are not intended to limit the scope of the disclosure. Although any methods and materials similar or equivalent to those described herein can be used in the practice for testing of the assembly, components, device(s) and methods herein disclosed, specific examples of appropriate materials and methods are described herein.

Modifications of the above-described modes for carrying out the device(s) and methods herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

A number of embodiments of the device(s) and methods herein disclosed have been described. Nevertheless, it will be understood that various modifications may be made without departing from the spirit and scope of the disclosure. Accordingly, other embodiments are within the scope of the following claims.

LIST OF CITED REFERENCES

[1] S. Iijima, Nature 354, 56 (1991).
[2] P. Avouris, J. Appenzeller, R. Martel, and S. Wind, Proc. IEEE 91, 1772 (2003).
[3] T. Rueckes, K. Kim, E. Joselevich, G. Y. Tseng, C. L. Cheung, and C. M. Lieber, Science 289, 94 (2000).
[4] V. Sazonova, Y. Yaish, H. Ustunel, D. Roundy, T. A. Arias, and P. L. McEuen, Nature 431, 284 (2004).
[5] R. J. Grow, Q. Wang, J. Cao, D. Wand and H. Dai, Appl. Phys. Lett. 86, 093104-1 (2005).
[6] C. Stampfer, T. Helbling, D. Obergfell, B. Schoberle, M. Tripp, A. Jungen, S. Roth, V. Bright, and C. Hierold, Nano. Lett. 6, 233 (2006).
[7] J. Kong, N. R. Franklin, C. Zhou, M. G. Chapline, S. Peng, K. Cho, and H. Dai, Science 287, 622, (2000).
[8] J. H. Leck, *Total and partial pressure measurement in vacuum systems*; Kluwer: Norwell, Mass. 1989.
[9] A. B. Kaul and H. M. Manohara, *Proc. of the 21$^{st}$ IEEE Internatl. Conf. on MEMS,* 156 (2008).
[10] A. Bachtold, M. Henny, C. Terrier, C. Strunk, C. Schonenberger, J.-P. Salvetat, J.-M. Bonard, and L. Forro, Appl. Phys. Lett. 73, 274 (1998).
[11] R. Martel, V. Derycke, C. Lavoie, J. Appenzeller, K. Chan, J. Tersoff, and P. Avouris, Phys. Rev. Lett. 87, 256805-1 (2001).
[12] M. Bockrath, D. Cobden, J. Lu, A. Rinzler, R. Smalley, L. Balents, and P. McEuen, Nature 397, 598 (1999).
[13] S. Tans, M. Devoret, H. Dai, A. Thess, R. Smalley, L. J. Geerligs, and C. Dekker, Nature 386, 474 (1997).
[14] J. Nygard, D. H. Cobden, M. Bockrath, P. L. McEuen, and P. E. Lindelof, Appl. Phys. A 69, 297 (1999).
[15] D. Mann, A. Javey, J. Kong, Q. Wang, and H. Dai, Nano. Lett. 3, 1541 (2003).
[16] A. Javey, J. Guo, M. Paulsson, Q. Wang, D. Mann, M. Lundstrom, and H. Dai, Phys. Rev. Lett. 92, 106804-1 (2004).
[17] J. Nygard and D. Cobden, Appl. Phys. Lett. 79, 4216 (2001).
[18] D. A. Walters, L. M. Ericson, M. J. Casavant, J. Liu, D. T. Colbert, K. A. Smith, and R. E. Smalley, Appl. Phys. Lett. 74, 3804 (1999).
[19] E. Pop, D. Mann, J. Cao, Q. Wang, K. Goodson, and H. Dai, Phys. Rev. Lett. 95, 155505 (2005).

The invention claimed is:

1. A sensing method comprising:
providing at least one carbon nanotube;
biasing the at least one carbon nanotube;
exposing the at least one carbon nanotube to an environment where gas is adapted to be detected, whereby, in presence of the gas, heat is removed by the gas from the at least one carbon nanotube;
varying pressure inside the environment with the gas, whereby temperature of the at least one carbon nanotube changes with variation of pressure; and
detecting variation in temperature of the at least one carbon nanotube as an electrical response.

2. The method of claim 1, wherein the method is a gas sensing method.

3. The method of claim 1, wherein the method is a chemical species sensing method to differentiate chemical species.

4. The method of claim 1, wherein each one of the at least one carbon nanotube is a single-walled carbon nanotube.

5. The method of claim 1, wherein biasing the at least one carbon nanotube occurs by connecting electrodes at end regions of the at least one carbon nanotube.

6. The method of claim 5, wherein the at least one carbon nanotube and the electrodes are suspended and devoid of a substrate.

7. The method of claim 6, wherein suspension occurs through critical point drying.

8. The method of claim 5, wherein the electrodes comprise metals selected from the group consisting of Al, Ti, Nb, Mo, Pd, Pt, Sc, Ta, W, Hf, Zr, Au, Cr and combinations thereof.

9. The method of claim 5, wherein the electrodes comprise metals selected from the group consisting of Au, Cr and combinations thereof.

10. The method of claim 6, wherein the electrodes comprise electrodes made of Cr.

11. The method of claim 1, wherein varying the pressure inside the environment with the gas comprises varying the pressure from a substantially ambient pressure to a substantially vacuum pressure.

12. The method of claim 1, wherein the variation in the temperature of the at least one carbon nanotube causes a resistance change in the at least one carbon nanotube, the resistance change being detected as a current response.

13. The method of claim 1, wherein the environment is a chamber containing the gas and the carbon nanotube.

14. The method of claim 1, wherein the at least one carbon nanotube is an array of carbon nanotubes.

15. The method of claim 1, wherein the at least one carbon nanotube is a bundle of carbon nanotubes.

16. The method of claim 1, wherein the at least one carbon nanotube is voltage biased and the electrical response is a current response.

17. The method of claim 1, wherein the electrical response is a voltage response.

* * * * *